(12) United States Patent
Sugimura

(10) Patent No.: US 6,551,336 B2
(45) Date of Patent: Apr. 22, 2003

(54) CORNEAL SURGICAL APPARATUS

(75) Inventor: Masahiro Sugimura, Aichi (JP)

(73) Assignee: Nidek Co., Ltd., Aichi (JP)

( * ) Notice: Subject to any disclaimer, the term of this patent is extended or adjusted under 35 U.S.C. 154(b) by 285 days.

(21) Appl. No.: 09/750,151

(22) Filed: Dec. 29, 2000

(65) Prior Publication Data

US 2001/0007943 A1 Jul. 12, 2001

(30) Foreign Application Priority Data

Jan. 6, 2000 (JP) ........................................ 2000-000630

(51) Int. Cl.[7] ................................................. A61F 9/007
(52) U.S. Cl. ............................................................ 606/166
(58) Field of Search ................................ 606/166, 167, 606/169, 180, 172, 107, 161, 171, 170; 464/3, 5, 6, 180

(56) References Cited

U.S. PATENT DOCUMENTS

| | | | |
|---|---|---|---|
| 4,662,370 A | 5/1987 | Hoffmann et al. ........... 128/305 |
| 4,903,695 A | 2/1990 | Warner et al. ................. 606/4 |
| RE35,421 E | 1/1997 | Ruiz et al. ................... 606/166 |
| 5,591,174 A | 1/1997 | Clark et al. ................. 606/130 |
| 5,595,570 A | 1/1997 | Smith ........................... 606/166 |
| 5,624,456 A | 4/1997 | Hellenkamp ................. 606/166 |
| 5,779,723 A | 7/1998 | Schwind ....................... 606/166 |
| 6,059,805 A | 5/2000 | Sugimura et al. ............ 606/166 |
| 6,083,236 A * | 7/2000 | Feingold ...................... 606/166 |
| 6,117,149 A * | 9/2000 | Sorensen et al. ............ 606/166 |
| 6,126,668 A * | 10/2000 | Bair et al. ................... 606/166 |
| 6,203,555 B1 * | 3/2001 | Amano et al. ............... 606/166 |
| 6,344,046 B2 * | 2/2002 | Sugimura et al. ............ 606/166 |

FOREIGN PATENT DOCUMENTS

| | | |
|---|---|---|
| EP | 0 956 840 | 11/1999 |
| EP | 1 033 120 | 9/2000 |

* cited by examiner

*Primary Examiner*—A. Vanatta
(74) *Attorney, Agent, or Firm*—Finnegan, Henderson, Farabow, Garrett & Dunner LLP

(57) ABSTRACT

A corneal surgical apparatus for incising a cornea of a patient's eye in a layered form includes: a blade; a rotating shaft; a bearing rotatably supporting the rotating shaft; a transmitting mechanism which converts rotation of the rotating shaft about a rotation center axis into oscillation in a direction perpendicular to the rotation center axis and transmits the oscillation to the blade; and a preventing mechanism which prevents moisture component from penetrating or infiltrating into a clearance between the rotating shaft and the bearing by controlling the rotation of the rotating shaft.

16 Claims, 4 Drawing Sheets

CORNEAL SURGICAL APPARATUS

BACKGROUND OF THE INVENTION

1. Field of the Invention

The present invention relates to a corneal surgical apparatus for incising the cornea of an eye of a patient in a layered form at the time of a keratorefrative surgery or the like.

2. Description of the Related Art

In recent years, attention has been focused on a LASIK (laser in situ keratomileusis) surgery for the keratorefractive surgery wherein a flap is formed by incising a corneal portion with a thickness of about 0.15 mm ranging from the corneal epithelium to the corneal stroma with a part of the cornea remaining connected like a hinge, ablating the corneal stroma in a refractive correction amount by an excimer laser light, and returning the flap to its original position. In the LASIK surgery, a corneal surgical apparatus called a microkeratome is used for incising the cornea in a layered form.

As a corneal surgical apparatus, one comprising a suction ring to be vacuum-fixed to a part of the cornea from a corneal ring portion to the surface of the conjunctiva, a cornea applanating member for applanating the cornea flatly, and a blade movable toward the hinge while being oscillated laterally so as to incise the flattened cornea into a layer form with a substantially uniform thickness, is known.

As a mechanism for the blade lateral oscillation, one comprising a motor, a rotation shaft to be rotated by the motor, a bearing rotatably supporting the rotation shaft, and a transmitting member, such as an eccentric pin, for converting the rotation of the motor transmitted through the rotation shaft into the lateral oscillation to be transmitted to the blade, is proposed. To incise the cornea uniformly and easily, the blade is required to be oscillated laterally at a high speed, and thus the motor rotates the rotation shaft at a high speed to rotate the eccentric pin on the rotation shaft at a high speed.

However, since the rotation shaft is required to laterally oscillate the relatively heavy blade and transmitting member through the eccentric pin, the rotation of the rotation shaft (i.e. the rotation at the blade side of the rotation shaft) is slightly varied or shifted. For this reason, liquid, such as ophthalmic solution (physiological saline) applied to the patient's eye during surgery and tear liquid, may penetrate or infiltrate into a small clearance between the rotation shaft and the bearing. This will cause erosion and short circuit of an electric system, and thus is not preferable.

SUMMARY OF THE INVENTION

In order to solve the above-noted problem, the present invention provides the following arrangements:

(1) A corneal surgical apparatus for incising a cornea of a patient's eye in a layered form, comprising:

a blade;

a rotating shaft;

a bearing rotatably supporting the rotating shaft;

transmitting means for converting rotation of the rotating shaft about a rotation center axis into oscillation in a direction perpendicular to the rotation center axis and transmitting the oscillation to the blade; and preventing means for preventing moisture component from penetrating into a clearance between the rotating shaft and the bearing by controlling the rotation of the rotating shaft.

(2) The apparatus of (1), wherein the preventing means includes correcting means for correcting rotation shift of the rotating shaft in the direction perpendicular to the rotation center axis.

(3) The apparatus of (2), wherein the correcting means causes the rotation shift of the rotating shaft entirely over and along the rotation center axis.

(4) The apparatus of (2), wherein the correcting means includes a weight member attached to at least one of an outer side of the rotating shaft and an inner side of the rotating shaft.

(5) The apparatus of (4), wherein the weight member is attached to the rotating shaft at a predetermined position opposite from a blade side of the rotating shaft.

(6) The apparatus of (1), wherein the transmitting means includes an eccentric pin that is projectingly provided on a blade side leading end of the rotating shaft and that is offset from the rotation center axis.

(7) The apparatus of (1), further comprising:

a liquid reservoir, provided to at least one of the rotating shaft and the bearing, for accumulating lubricant applied to the clearance between the rotating shaft and the bearing.

(8) The apparatus of (1), further comprising:

a drive unit for rotating the rotating shaft.

(9) The apparatus of (1), further comprising:

translating means for moving the blade in an incise direction.

(10) The apparatus of (9), wherein the translating means includes a drive unit for moving the rotating shaft in an incise direction.

(11) A corneal surgical apparatus for incising a cornea of a patient's eye in a layered form, comprising:

a blade;

a rotating shaft having a blade side close to the blade and an opposite side opposite from the blade with respect to the blade side, wherein a center of gravity of the opposite side is offset from a rotation center axis of the rotating shaft;

a bearing rotatably supporting the rotating shaft;

an eccentric pin that is projectingly provided on a blade side leading end of the rotating shaft and that is offset from the rotation center axis; and a transmitting member having a groove engaged with the eccentric pin, the transmitting member being supported movably in a direction perpendicular to the rotation center axis.

(12) The apparatus of (11), wherein the center of gravity of the opposite side of the rotating shaft is offset to have a predetermined relationship with respect to an offset position of the eccentric pin.

(13) The apparatus of (11), wherein a weight member is provided to the rotating shaft so that the weight member is located on at least one of an inner side of the rotating shaft and an outer side of the rotating shaft and on the opposite side.

(14) The apparatus of (11), wherein at least one of the rotating shaft and the bearing have a liquid reservoir for accumulating lubricant applied to the clearance between the rotating shaft and the bearing.

(15) A transmitting mechanism, in a corneal surgical apparatus, for converting inputted rotation into oscillation and transmitting the oscillation to a blade, the transmitting mechanism comprising:

a rotating shaft having a first side to which the rotation is inputted and a second side opposite from the first side;

a bearing rotatably supporting the rotating shaft;

a first, discrete unbalance component provided to the first side, and a second, discrete unbalance component provided to the second side.

(16) The mechanism of (15), wherein the first component includes a weight member, and the second component includes an eccentric pin.

The present disclosure relates to the subject matter contained in Japanese patent application No. 2000-630 (filed on Jan. 6, 2000), which is expressly incorporated herein by reference in its entirety.

DESCRIPTION OF THE PREFERRED EMBODIMENT

Figure 1:
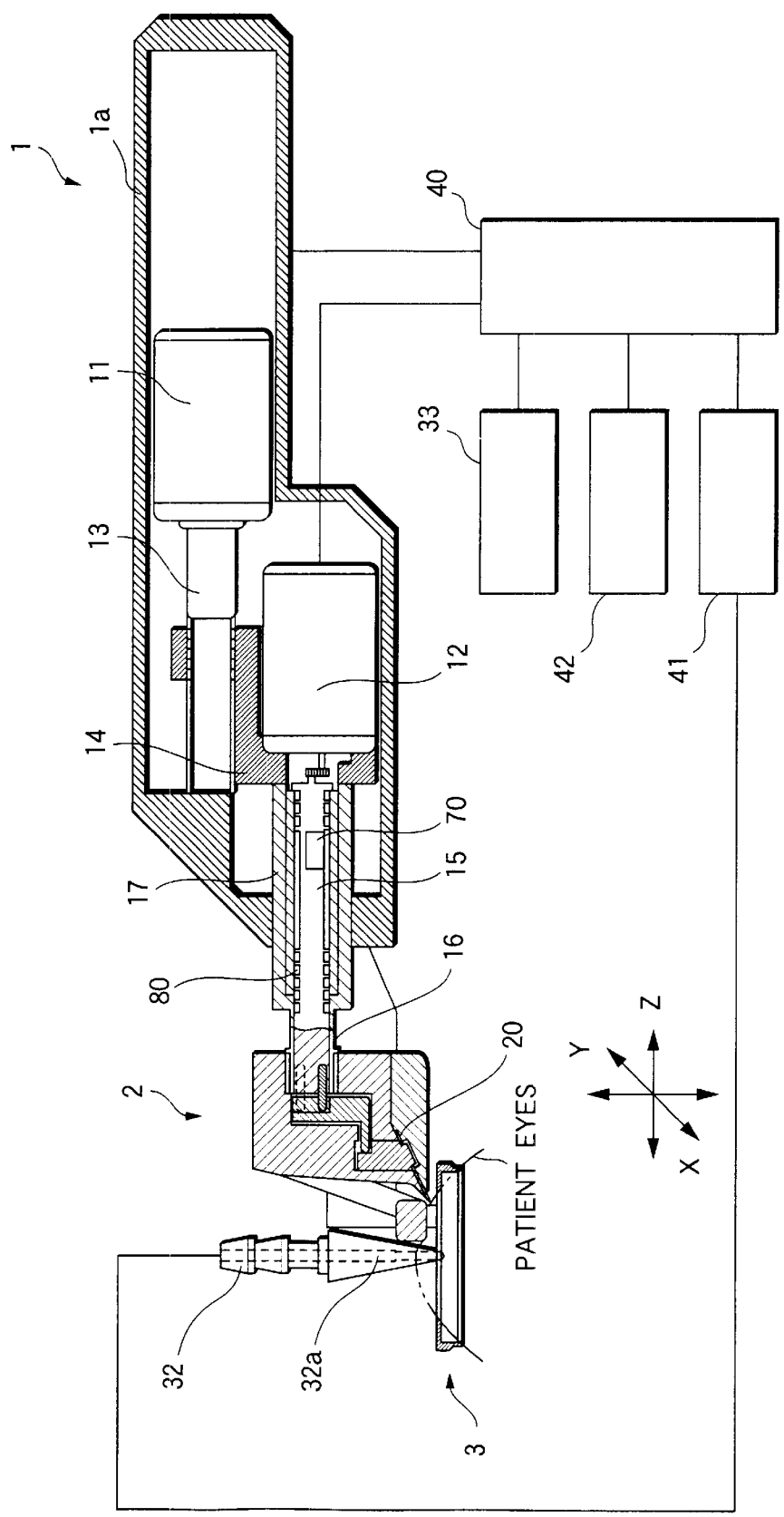
FIG. 1 is a cross-sectional view and a control system diagram of a corneal surgical apparatus in accordance with an embodiment of the present invention.

Referring to the accompanying drawings, a description will be given of an embodiment of the present invention. FIG. 1 is a cross-sectional view and a control system diagram of a corneal surgery apparatus in accordance with an embodiment of the present invention.

Reference numeral 1 denotes a main body of the corneal surgery apparatus(microkeratome), and reference numeral 1a denotes a grip to be held by an operator during the surgery. A suction unit 3 for fixing the apparatus to the patient's eye and a cutting unit 2, which has a blade 20 (which will be described later) for incising the cornea and is adapted to move rectilinearly on the suction unit 3, are provided on the front side (left-hand side in the drawing) of the main body 1.

Figure 5:
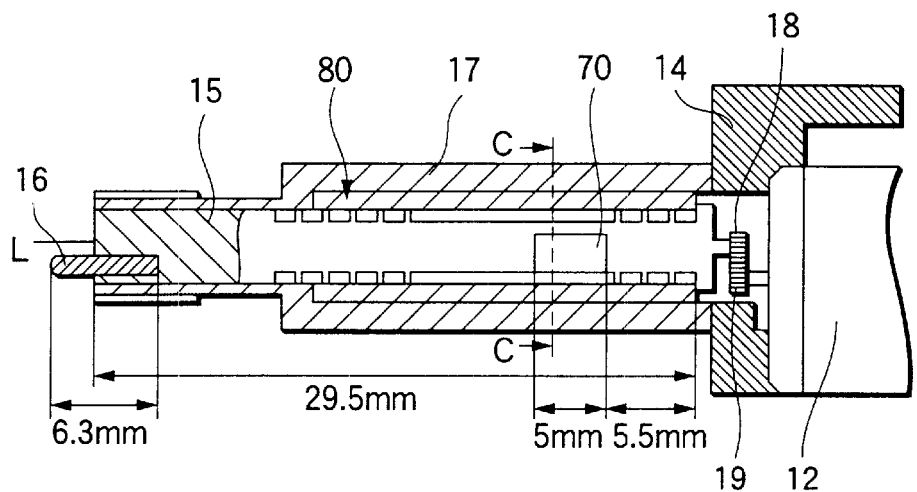
FIG. 5 is an explanatory diagram illustrating a weight member attached to a rotating shaft.

A feed motor 11 for rectilinearly moving (translating) the cutting unit 2 in the incising direction (in the Z direction) and an oscillating motor 12 for imparting oscillations in the lateral direction (in the X direction) to the blade 20 are installed in the main body 1. A feed screw 13 is coupled to a rotating shaft of the motor 11, which has a threaded portion corresponding in length to the rectilinear movement (translation) or travel of the cutting unit 2. An attaching member 14 is threadedly engaged with the screw 13. The motor 12 as well as a connecting member 17 are fixed to the attaching member 14. As the motor 11 is rotated forwardly or reversely, the motor 12 and the connecting member 17 move forwardly or backwardly (in the Z direction) through the screw 13 and the attaching member 14, thereby causing the cutting unit 2 to move forwardly or backwardly. Further, the connecting member 17 serves also as a bearing or rotational support for a rotating shaft 15 so that the rotating shaft 15 is rotatably held by the connecting member 17. A pinion 18 fixed to the rotating shaft 15 is meshed with a pinion 19 fixed to the rotating shaft of the motor 12, so that the rotating shaft 15 is rotated by the motor 12 (see FIG. 5). An eccentric pin 16 is embedded or protruded on a distal end of the rotating shaft 15 at a position offset from the center of rotation, and the eccentric pin 16 imparts lateral oscillations to the blade 20 (which will be described later). Reference numeral 70 denotes a weight member attached to the rotating shaft 15.

A lubricant, such as a lubricating oil, is applied to a clearance between the rotating shaft 15 and the connecting member 17 to make the high speed rotation (9,000 to 10,000 rpm in the present embodiment) of the rotating shaft 15 smooth. The lubricant can eliminate friction heat and friction particles generated due to friction between the rotating shaft 15 and the connecting member 17 which are relatively rotated at a high speed. Reference numeral 80 denotes a liquid reservoir provided to the rotating shaft 15, which accumulates the lubricant therein, thereby securing the smooth rotation of the rotating shaft 15, eliminating the leakage of the lubricant and preventing external moisture components, such as ophthalmic solution, from penetrating or infiltrating into the clearance.

Figure 2:
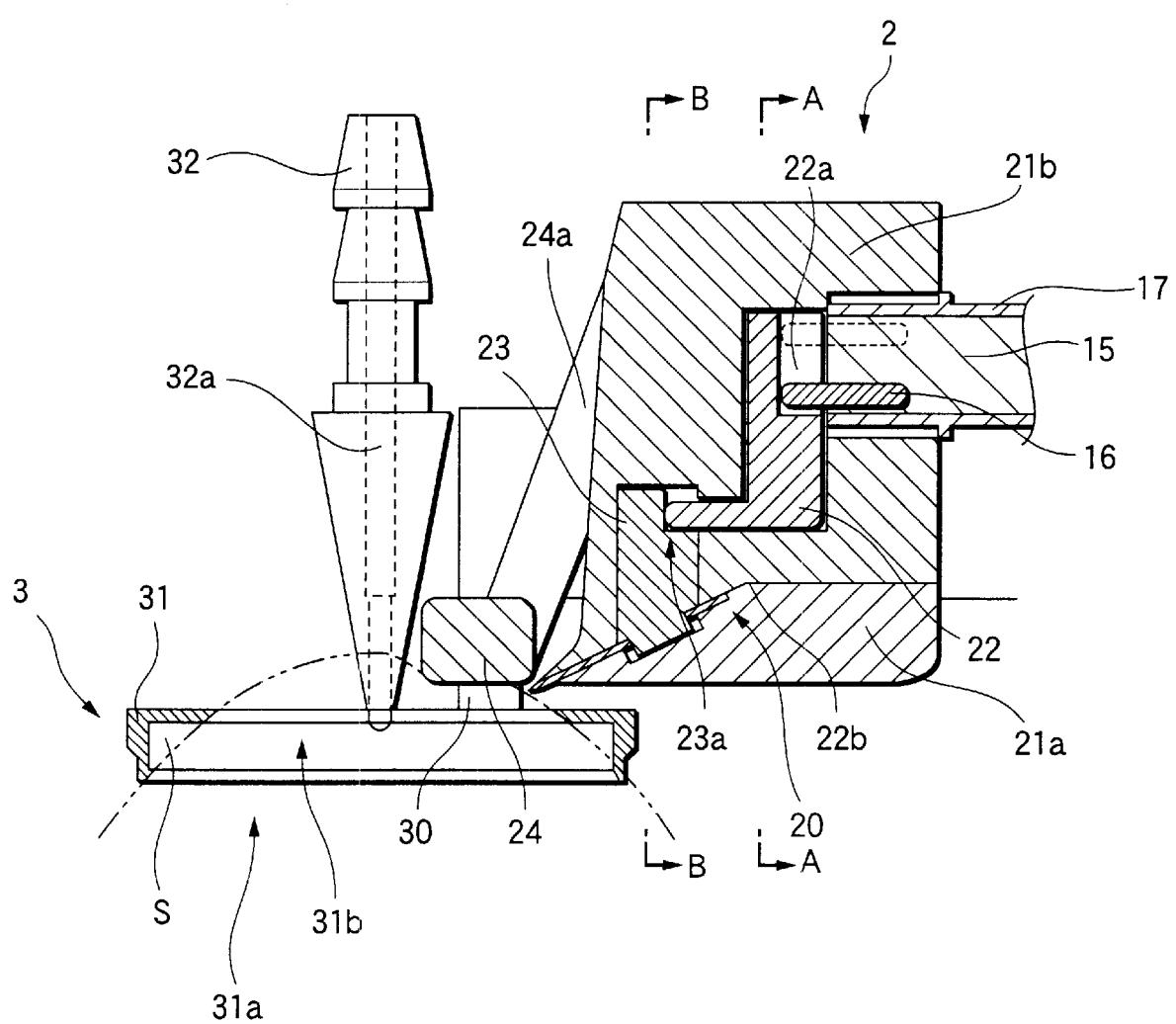
FIG. 2 is an enlarged explanatory diagram of a cutting unit and a suction unit of the apparatus.
Figure 3:
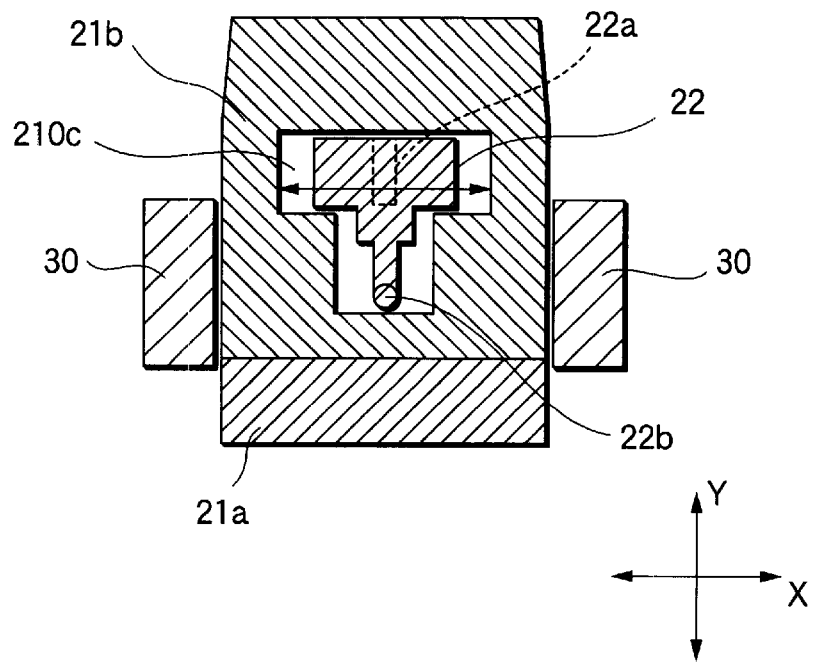
FIG. 3 is a cross-sectional view, taken along line A—A of FIG. 2, illustrating the cutting unit.
Figure 4:
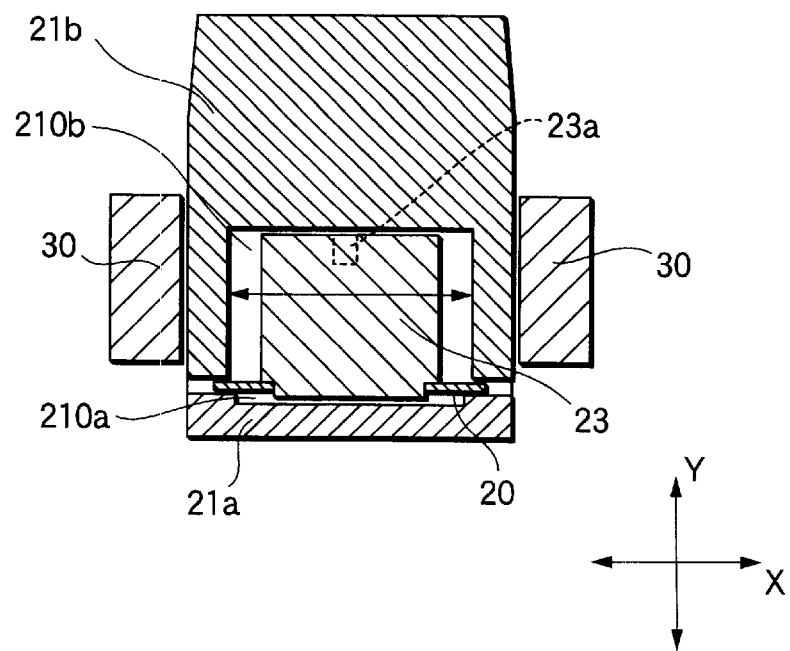
FIG. 4 is a cross-sectional view, taken along line B—B of FIG. 2, illustrating the cutting unit.

Referring next to FIGS. 2, 3 and 4, a description will be given of the arrangements of the cutting unit 2 and the suction unit 3. FIG. 2 is an enlarged view of the cutting unit 2 and the suction unit 3 shown in FIG. 1. FIG. 3 is a cross-sectional view taken along line A—A of FIG. 2. FIG. 4 is a cross-sectional view taken along line B—B of FIG. 2.

The cutting unit 2 is comprised of the blade 20 for corneal incision; a blade holder 21a and a holder block 21b for holding the blade 20 in such a manner as to permit lateral oscillations; a first oscillation transmitting member 22 for transmitting the lateral oscillations generated by the eccentric pin 16; a second oscillation transmitting member 23 for transmitting the lateral oscillations by the first transmitting member 22 to the blade 20, and a cornea applanating member 24 fixed to the block 21b by means of an attaching member 24a. A rotation hole into which the rotating shaft 15 is inserted is provided inside the block 21b, and a tip portion of the connecting member 17 is fixed thereto.

A metal blade having a blade edge of stainless steel, steel, or the like or a mineral blade having a blade edge of diamond, sapphire or the like is used as the blade 20. The blade 20 is held between the holder 21a and the block 21b at an appropriate angle with respect to the horizontal plane in such a manner as to be capable of undergoing lateral oscillations. On the holder 21a side, a shallow recess 210a is formed at a portion where the blade 20 is placed, and the lateral width of the recess 210a is set to be larger than the oscillating width for the lateral oscillations of the blade 20.

The first transmitting member 22 is movable in the lateral direction (in the X direction) within a receiving groove 210c formed in the block 21b. The upper and lower portions of the first transmitting member 22 in the vertical direction (in the Y direction) is held by the block 21b. A vertical groove 22a for engagement with the eccentric pin 16 is formed in the first transmitting member 22. When the rotating shaft 15 is rotated by the rotative driving of the motor 12, the eccentric pin 16 engaged with the vertical groove 22a applies a lateral driving force to the first transmitting member 22. This causes the first transmitting member 22 to oscillate laterally.

The second transmitting member 23 is movable in the lateral direction (in the X direction) within the receiving groove 210b formed in the block 21b. The upper portion and the lower portion of the second transmitting member 23 are respectively held by the block 21b and the blade holder 21a.

The first transmitting member 22 is provided at its lower portion with a protrusion 22b projected to the blade 20 side, and the second transmitting member 23 is formed with a vertical groove 23a engaged with the protrusion 22b. As the first transmitting member 22 is oscillated laterally by the rotation of the rotating shaft 15 (circumferential or circular motion of the eccentric pin 16), the protrusion 22b engaged with the vertical groove 23a is laterally oscillated, thereby applying lateral kinematics force to the second transmitting member 23. Accordingly, the second transmitting member 23 is laterally oscillated together with the blade 20 fixed to the second transmitting member 23.

The cornea applanating member 24 is provided on the front side (left-hand side in FIG. 2) of the blade 20 so as to flatly applanate the cornea of the patient's eye in advance of the corneal incision by the blade 20 as the cutting unit 2 is moved forwardly. Since the blade 20 incises the cornea thus applanated flatly by the applanating member 24, a flap of a uniform layer is formed.

In this embodiment, the distance between the edge of the blade 20 attached to the holder 21a and the lower surface of the applanating member 24 is set to be about 0.15 mm so that the cornea can be incised with this thickness in a layered form.

The apparatus is designed so that the rotating shaft 15 is rotated about a central axis L (see FIG. 5) by rotative driving of the motor 12. However, since the rotating shaft 15 laterally oscillates the first transmitting member 22, the second transmitting member 23 and the blade 20 through the eccentric pin 16, the rotation of the rotating shaft 15 in the blade 20 side is varied or shifted in a direction perpendicular to the rotation axis L (that is, the rotating shaft 15 makes a circular motion about the central axis L while being rotated). More specifically, the eccentric pin 16 makes a circular motion by the rotation of the rotating shaft 15, and periodically collides against a side wall of the vertical groove 22a to push the first transmitting member 22 right or left in the lateral direction. When the eccentric pin 16 pushes the first transmitting member 22 right or left, the eccentric pin 16 receives a reaction therefrom so that the eccentric pin 16 and thus the rotating shaft 15 is shifted in the opposite direction. This shift of the rotating shaft 15 is larger as a weight of a component(s) to be laterally oscillated by the eccentric pin 16 is larger. This shift causes the moisture component, such as ophthalmic solution, penetrating into the recess 210a and the receiving grooves 210b and 210c, to further penetrate into the small clearance between the rotating shaft 15 and the connecting member 17.

To avoid the penetrating of the moisture component as described above, the weight member 70 is attached to the rotating shaft 15 at a predetermined position close to the motor 12 and away from the blade 20 (in the motor 12 side opposite from the blade 20 side). The weight member 70 attached in this manner serves such that the load by the reaction from the first transmitting member 22, which acts on the eccentric pin 16 side (the blade 20 side) of the rotating shaft 15, and the load by a centrifugal force of the weight member 70, which acts on the motor 12 side of the rotating shaft 15, are balanced to each other in a direction perpendicular to the rotation axis L, thereby causing the rotation shift entirely over and along the rotation axis L. This prevents the penetrating of the moisture component into the clearance between the rotating shaft 15 and the connecting member 17. However, note that if the rotation shift on the motor 12 side is excessively large, the lubricant between the rotating shaft 15 and the connecting member 17 may be leaked externally, and therefore it is important to set the rotation shift on the motor 12 side to be balanced with the rotation shift on the eccentric pin 16 side.

Figure 6:
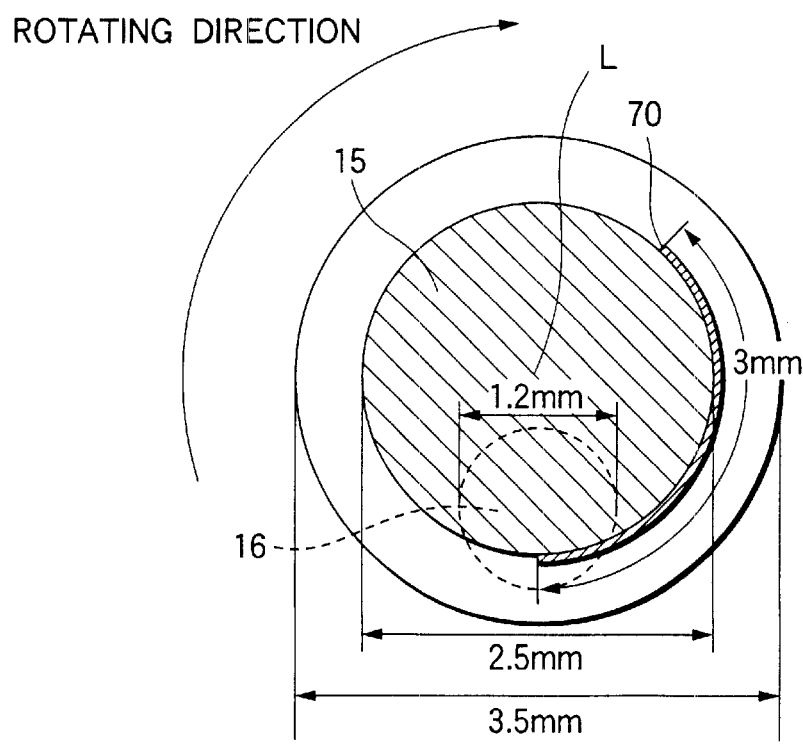
FIG. 6 is a cross-sectional view, taken along line C—C of FIG. 5, illustrating the weight member.

The weight, size and attached position of the weight member 70 for balancing the rotation shift are determined depending on a length of the rotating shaft 15, weight and position of the eccentric pin 16, weight of the blade 20 and each transmitting member, etc. In this embodiment, the weight member 70 is attached at the predetermined position shown in FIGS. 5 and 6, and the weight of the weight member 70 is 5.5 mg (the weight of the eccentric pin 16 is 56 mg, the weight of the blade 20 and the second transmitting member 23 is 0.3 g and the weight of the first transmitting member 22 is 0.3 g). In addition, the weight member 70 may be provided inside the rotating shaft 15 (that is, it suffices that the weight member 70 offsets a center of gravity of the rotating shaft 15 from a rotation center of the rotating shaft 15).

The suction unit 3 includes a fixing member 30, a suction ring 31, and a suction pipe 32. The suction ring 31 is fixed to the main body 1 by the fixing member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye in place for surgery, the cornea of the patient's eye projects upward from the opening 31b, and a lower end portion of the suction ring 31 and an opening end portion (a periphery) of the opening 31b are caused to abut against the patient's eye to define a space S for suction.

The suction pipe 32 is embedded on (i.e. projectingly provided on) the suction ring 31, and connected through an unillustrated vacuum tube to a pump 41. A suction passage 32a provided inside the suction pipe 32 communicates with the recessed portion 31a, and as the air inside the space S is sucked and discharged by the pump 41 through the passage 32a, the suction ring 31 is vacuum-fixed to the patient's eye. In this fixation, as the operator holds the main body 1, the positioning of the opening 31b can be facilitated, and the apparatus can be held stably.

In addition, an unillustrated pressure detection pipe is embedded on the suction ring 31, and the pressure detection pipe is connected to a pressure detector 33 through an unillustrated tube. The detector 33 detects, through the pressure detection pipe, the air pressure inside the space S sucked by the pump 41. A control unit 40 controls the operation of the motor 11, the motor 12, the pump 41, etc. on the basis of the air pressure detected by the detector 33.

Hereafter, a description will be given of the operation of the apparatus having the above-described configuration. While confirming the state of inclination of the suction ring 31 (main body 1), the position of the pupillary center, and the like on the basis of a mark that has been preliminarily applied on the patient's cornea using an instrument such as a marker, the operator aligns the center of the opening 31b with the pupillary center, and disposes the suction ring 31 on the patient's eye.

After installation of the suction ring 31, the operator, while keeping the position and the posture of the main body 1, operates the pump 41 to suck the air in the space S between the suction ring 31 and the patient's eye to thereby decrease the air pressure (toward the negative pressure). When the air pressure in the space S is decreased to a fixed value (when it reaches a sufficient negative pressure), the operation of the pump 41 is controlled by a control unit 40 so as to maintain that air pressure. Accordingly, the suction ring 31 is vacuum-fixed onto the patient's eye.

Upon completion of the fixing of the apparatus, the operator operates the foot switch 42 to rotatively drive the motor 11 and the motor 12. Upon reception of the drive instruction signal by the foot switch 42, the control unit 40 controls the rotational driving of the motor 12 so that the blade 20 is oscillated laterally at a fixedly set or variably set oscillating speed.

The control unit 40 controls the rotational driving of the motor 11 so that the cutting unit 2 is rectilinearly moved (translated) toward the hinge (in the incise direction) at a fixedly set or variably set feeding speed. Concurrently, the rotating shaft 15 slides in the advancing direction integrally with the cutting unit 2 while making rotational motion for imparting lateral oscillations to the blade 20.

When the flap formation is complete, that is, the edge of the blade 20 has incised the cornea with the hinge portion left, the motor 11 is rotated reversely to return the cutting unit 2 to its initial position. For this return operation, the rotation of the motor 12 is stopped using the independent control of the motors 11 and 12, to thereby withdraw or remove the blade 20 from the flap while avoiding the unnecessary oscillation of the blade 20. This reduces the possibility that the flap thus formed is cut off during the course of the return operation.

After the cutting unit 2 is returned to its initial position, the air is introduced into the space S to release the suction, and the apparatus (the suction ring 31) is removed. Subsequently, a refractive correction amount of the corneal stroma is ablated and removed using excimer laser light, and then the flap is returned to its original position, thereby completing the surgery.

Although the motor is used to rotate the rotating shaft in this embodiment, an air turbine or the like may be used to rotate the rotating shaft.

Although a blade translating (feeding) mechanism is designed to linearly move the blade in the incise direction to incise the cornea, the blade translating (feeding) mechanism may be designed to rotatingly move the blade to incise the cornea.

As described above, according to the present invention, it is possible to prevent the moisture component from penetrating or infiltrating into the clearance between the rotating shaft and the bearing without complicating the structure.

What is claimed is:

1. A corneal surgical apparatus for incising a cornea of a patient's eye in a layered form, comprising:
   a blade;
   a rotating shaft;
   a bearing rotatably supporting the rotating shaft;
   transmitting means for converting rotation of the rotating shaft about a rotation center axis into oscillation in a direction perpendicular to the rotation center axis and transmitting the oscillation to the blade; and
   preventing means for preventing moisture component from penetrating into a clearance between the rotating shaft and the bearing by controlling the rotation of the rotating shaft.

2. The apparatus of claim 1, wherein the preventing means includes correcting means for correcting rotation shift of the rotating shaft in the direction perpendicular to the rotation center axis.

3. The apparatus of claim 2, wherein the correcting means causes the rotation shift of the rotating shaft entirely over and along the rotation center axis.

4. The apparatus of claim 2, wherein the correcting means includes a weight member attached to at least one of an outer side of the rotating shaft and an inner side of the rotating shaft.

5. The apparatus of claim 4, wherein the weight member is attached to the rotating shaft at a predetermined position opposite from a blade side of the rotating shaft.

6. The apparatus of claim 1, wherein the transmitting means includes an eccentric pin that is projectingly provided on a blade side leading end of the rotating shaft and that is offset from the rotation center axis.

7. The apparatus of claim 1, further comprising:
   a liquid reservoir, provided to at least one of the rotating shaft and the bearing, for accumulating lubricant applied to the clearance between the rotating shaft and the bearing.

8. The apparatus of claim 1, further comprising:
   a drive unit for rotating the rotating shaft.

9. The apparatus of claim 1, further comprising:
   translating means for moving the blade in an incise direction.

10. The apparatus of claim 9, wherein the translating means includes a drive unit for moving the rotating shaft in an incise direction.

11. A corneal surgical apparatus for incising a cornea of a patient's eye in a layered form, comprising:
    a blade;
    a rotating shaft having a blade side close to the blade and an opposite side opposite from the blade with respect to the blade side, wherein a center of gravity of the opposite side is offset from a rotation center axis of the rotating shaft;
    a bearing rotatably supporting the rotating shaft;
    an eccentric pin that is projectingly provided on a blade side leading end of the rotating shaft and that is offset from the rotation center axis; and
    a transmitting member having a groove engaged with the eccentric pin, the transmitting member being supported movably in a direction perpendicular to the rotation center axis.

12. The apparatus of claim 11, wherein the center of gravity of the opposite side of the rotating shaft is offset to have a predetermined relationship with respect to an offset position of the eccentric pin.

13. The apparatus of claim 11, wherein a weight member is provided to the rotating shaft so that the weight member is located on at least one of an inner side of the rotating shaft and an outer side of the rotating shaft and on the opposite side.

14. The apparatus of claim 11, wherein at least one of the rotating shaft and the bearing have a liquid reservoir for accumulating lubricant applied to the clearance between the rotating shaft and the bearing.

15. A transmitting mechanism, in a corneal surgical apparatus, for converting inputted rotation into oscillation and transmitting the oscillation to a blade, the transmitting mechanism comprising:
    a rotating shaft having a first side to which the rotation is inputted and a second side opposite from the first side;
    a bearing rotatably supporting the rotating shaft;
    a first, discrete unbalance component provided to the first side, and
    a second, discrete unbalance component provided to the second side.

16. The mechanism of claim 15, wherein the first component includes a weight member, and the second component includes an eccentric pin.

* * * * *